US012721667B2

(12) United States Patent
Ko

(10) Patent No.: US 12,721,667 B2

(45) Date of Patent: Sep. 1, 2026

(54) TREATMENT APPARATUS FOR DENATURING TISSUE USING RF ENERGY, CONTROL METHOD THEREOF, AND TREATMENT METHOD USING THE SAME

(71) Applicant: LUTRONIC CORPORATION, Goyang-si (KR)

(72) Inventor: Kwangchon Ko, Goyang-si (KR)

(73) Assignee: LUTRONIC CORPORATION, Goyang-si (KR)

( * ) Notice: Subject to any disclaimer, the term of this patent is extended or adjusted under 35 U.S.C. 154(b) by 237 days.

(21) Appl. No.: 18/406,631

(22) Filed: Jan. 8, 2024

(65) Prior Publication Data

US 2024/0238035 A1 Jul. 18, 2024

(30) Foreign Application Priority Data

Jan. 12, 2023 (KR) ........................ 10-2023-0004910
Oct. 26, 2023 (KR) ........................ 10-2023-0144571
Dec. 11, 2023 (KR) ........................ 10-2023-0178596

(51) Int. Cl.
*A61B 18/14* (2006.01)
*A61B 18/00* (2006.01)

(52) U.S. Cl.
CPC .... *A61B 18/14* (2013.01); *A61B 2018/00041* (2013.01); *A61B 2018/00464* (2013.01); *A61B 2018/00732* (2013.01); *A61B 2018/00738* (2013.01)

(58) Field of Classification Search
CPC .......... A61B 18/14; A61B 2018/00041; A61B 2018/00464; A61B 2018/00732; A61B 2018/00738
See application file for complete search history.

(56) References Cited

U.S. PATENT DOCUMENTS 8,700,176 B2 * 4/2014 Azar ...................... A61B 18/14 607/101
9,198,735 B2 * 12/2015 Taghizadeh ............ A61B 90/37
2008/0183251 A1 7/2008 Azar et al.
2021/0146119 A1 * 5/2021 Prouza ................ A61N 5/0616
2021/0204996 A1 * 7/2021 Ko .......................... A61N 1/06
2021/0268299 A1 * 9/2021 Casalino .............. A61M 37/00
(Continued)

FOREIGN PATENT DOCUMENTS

EP 4 166 188 A1 4/2023
EP 4 400 156 A1 7/2024
(Continued)

OTHER PUBLICATIONS

The Extended European Search Report for European Patent Application No. 24219031.2, dated Apr. 8, 2025.

*Primary Examiner* — Michael F Peffley

(57) ABSTRACT

Disclosed are a treatment apparatus for denaturing tissue using RF energy having multiple frequencies, a control method thereof, and a treatment method using the same, in which skin treatment is performed using the RF energy with multiple-frequencies different in depth of delivering the RF energy into the tissue. The frequencies of the RF energy may be modulated by the RF modulator. Additionally, the operation of one of several RF generators, which can generate RF energy at the frequency of the RF energy, is determined by the selection of one among multiple RF generators.

19 Claims, 26 Drawing Sheets

(56) References Cited

U.S. PATENT DOCUMENTS

| | | | | |
|---|---|---|---|---|
| 2022/0314015 | A1* | 10/2022 | Bartholomeusz .... | A61N 1/0492 |
| 2023/0123145 | A1 | 4/2023 | Ko | |

FOREIGN PATENT DOCUMENTS

| | | | |
|---|---|---|---|
| JP | 2023-79985 | A | 6/2023 |
| JP | 2023-111562 | A | 8/2023 |
| KR | 10-0706155 | B1 | 4/2007 |
| KR | 10-2014-0011319 | A | 1/2014 |
| KR | 10-2022-0136112 | A | 10/2022 |
| KR | 10-2023-0054086 | A | 4/2023 |
| KR | 10-2538213 | B1 | 6/2023 |

* cited by examiner

TREATMENT APPARATUS FOR DENATURING TISSUE USING RF ENERGY, CONTROL METHOD THEREOF, AND TREATMENT METHOD USING THE SAME

CROSS REFERENCE TO RELATED APPLICATIONS

This application is based on and claims priority under 35 U.S.C. § 119 to Korean Patent Application No. 10-2023-0004910 filed on Jan. 12, 2023, Korean Patent Application No. 10-2023-0144571 filed on Oct. 26, 2023 and Korean Patent Application No. 10-2023-0178596, Dec. 11, 2023 in the Korean Intellectual Property Office, the disclosure of which is incorporated by reference herein in its entirety.

BACKGROUND OF THE INVENTION

Field of the Invention

The present disclosure relates to a treatment apparatus for denaturing tissue using RF (Radio-Frequency) energy and control method for that.

Description of the Related Art

Devices for delivering RF energy to tissue for therapeutic purposes have been developed in various manners. In particular, devices that cause appropriate degeneration of the skin using RF energy and exert a skin treatment effect through tissue regeneration have recently been developed.

Korean Patent No. 0706155 is disclosed in relation to a conventional treatment device using RF energy. This conventional device has a problem of low treatment efficiency because the skin is treated using RF energy at a fixed frequency.

SUMMARY OF THE INVENTION

To solve the aforementioned problem, the present disclosure provides a treatment apparatus for denaturing tissue using RF energy which can adjust the frequency of RF energy in response to the depth and temperature of tissue, a control method thereof.

In an aspect, there is provided a treatment device using RF energy which can adjust RF energy to multiple frequencies and delivering the RF energy during one-time treatment.

Multiple frequencies of RF energy may include at least three frequencies for different heating depths within the tissue.

Additionally, RF energy may be delivered to the tissue according to a pulse train, and the frequency of selecting a frequency of the RF energy may be controlled through the pulse train on the basis of at least one of an elapsed time of treatment, a tissue temperature, or a treatment mode.

Additionally, according to the present disclosure, a method of controlling a skin treatment device for denaturing tissue using multi-frequency RF energy is provided.

Additionally, according to the present disclosure, there is provided a method of denaturing tissue by configuring a pulse train with frequencies for different heating depths in skin tissue and delivering RF energy to the tissue according to the pulse train. The method of denaturing tissue can improve treatment efficiency by adjusting the frequency of delivering RF energy to the epidermis layer, dermis layer, and fat layer on the basis of least one of an elapsed time of treatment, the temperature of tissue or skin surface, and a treatment mode.

According to the skin treatment device for denaturing tissue using multi-frequency RF energy, the control method thereof, and the method of denaturing tissue using the same according to the present disclosure, it is possible to induces regeneration for producing new collagen fibers by denaturing the epidermis and dermis with RF energy and to remodeling the skin contour by killing fat cells with the RF energy.

DETAILED DESCRIPTION OF THE INVENTION

Figure 1:
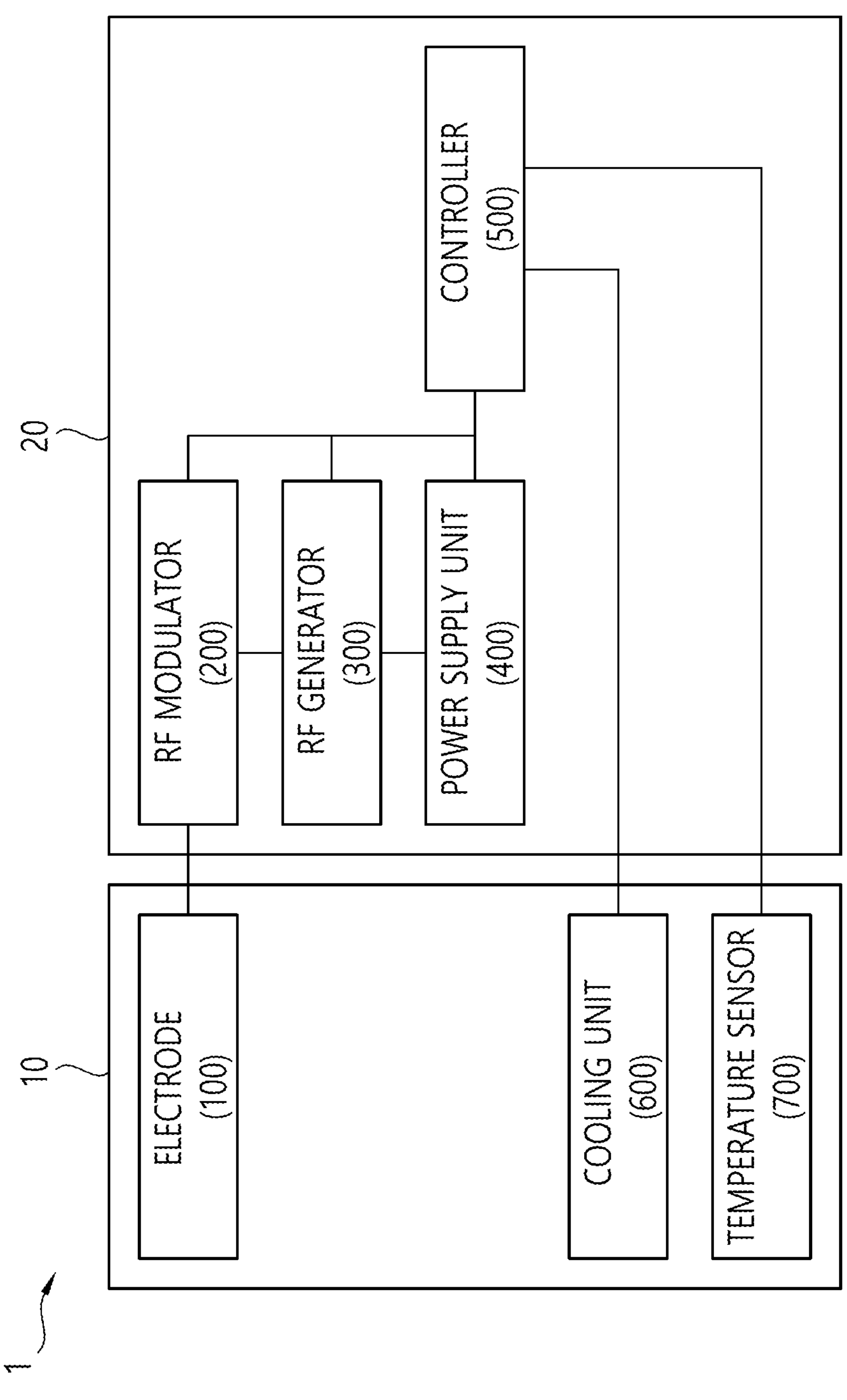
FIG. 1 is a block diagram showing a configuration of a skin treatment device for denaturing tissue using multi-frequency RF energy according to a first embodiment of the present disclosure.

Hereinafter, a skin treatment device for denaturing tissue using multi-frequency RF energy, a control method thereof according to embodiments of the present disclosure will be described in detail with reference to the attached drawings. In the description of the following embodiments, the name of each component may be referred to as different names in the art. However, if there is functional similarity and identity between components, they can be regarded as equivalent components even if modified embodiments are adopted. Additionally, a symbol is attached to each component for convenience of description. However, content shown in the drawings in which such symbols are written does not limit each component to the scope within the drawings. Likewise, even if an embodiment in which a configuration in a drawing is partially modified is adopted, it can be regarded as an equivalent configuration if there is functional similarity and identity. Further, if a component is recognized as a component that should be included in light of the general level of technicians in the relevant technical field, the description thereof will be omitted.

The present disclosure will be described on the premise that treatment means heating the skin tissue to improve wrinkles, tone and textural changes, scars and acne scarring, sagging mucosa, overall rejuvenation, hyperhidrosis, laxity, lifting, tightening, fat reduction, etc., and treatment means heating and killing fat cells to prevent additional fat accumulation.

Furthermore, in this specification, the term 'tissue' can refer to facial skin tissue. Additionally, 'tissue' may encompass skin tissue from various parts of the human body such as the abdomen and thighs. According to the embodiments disclosed herein, when treating facial skin tissue, positive effects such as improvement in wrinkles as mentioned earlier, and enhancement of facial contour through the apoptosis of fat cells can be achieved. Improvement in facial contour implies a change in the shape or appearance of the face, contributing to positive outcomes for the patient, such as a favorable impression or a more youthful appearance.

FIG. 1 is a block diagram showing a configuration of a skin treatment device for denaturing tissue using multi-frequency RF energy according to a first embodiment of the present disclosure.

Referring to FIG. 1, the skin treatment device 1 for denaturing tissue using multi-frequency RF energy according to the first embodiment of the present disclosure includes a main body 2 and a handpiece 10. The main body 2 includes elements for generating and controlling RF energy, and the handpiece 10 is configured to deliver RF energy to tissue. The main body 20 may include a power supply unit 400, an RF generator 300, an RF modulator 200, and a controller 500. The handpiece 10 may include an electrode 100, a temperature sensor 600, and a cooling unit 700. Although not shown, the handpiece 10 and the main body 20 may be connected by a cable to deliver and receive RF energy and various signals for control. Additionally, the handpiece 10 and/or the main body 20 may further include a display (not shown) for displaying various types of information related to operation and treatment and receiving commands from a user.

The RF generator 300 may be configured to receive power from the power supply unit 400 and to generate RF energy. The RF modulator 200 is configured to control at least one of the frequency, power, voltage, or electric power of the RF energy generated by the RF generator 300. Meanwhile, a well-known circuit configuration may be applied to the power supply unit 400, the RF generator 300, and the RF modulator 200.

The electrode 100 is electrically connected to the RF modulator 200 and is configured to receive RF energy. The electrode 100 is configured to be exposed at the end of the handpiece and can be configured to deliver RF energy to tissue at the time of coming into contact with the tissue. A plurality of electrodes 100 may be provided and arranged in a predetermined pattern. At least a portion of the electrode 100 may be configured as a flat surface to non-invasively deliver RF energy to the tissue. The electrode 100 may serve as a bipolar electrode or a monopolar electrode.

The cooling unit 600 may be configured to prevent excessive damage to the tissue when RF energy is delivered to the tissue to heat the tissue. The cooling unit 600 may cool the rear of the electrode in contact with the tissue or may directly cool the skin tissue. The cooling unit 600 may spray coolant to cool the electrode and/or the tissue through the heat of vaporization of the coolant. Additionally, the cooling unit 600 may selectively bring a heat sink into contact with the electrode and/or tissue to cool the electrode and/or the tissue in a conductive manner. Further, the cooling unit 600 may be configured as an air cooling type to force air to flow inside the handpiece. However, the configurations of the cooling unit 600 described above are merely examples and may be modified and applied as various configurations in which the cooling power is actively adjusted according to the configuration of the controller 500.

The temperature sensor 700 is configured to measure temperature at a plurality of points while RF energy is delivered to tissue. The temperature sensor 700 may include a plurality of temperature sensors. The plurality of temperature sensors may be configured to measure temperature at a plurality of points in a treatment area to which RF energy is delivered.

The controller 500 controls the RF modulator 200 to adjust the frequency or pulse width of RF energy. The controller 500 configures a pulse train and delivers multi-frequency RF energy through a sequence. Additionally, the controller 500 may control the RF generator 300 to block RF energy upon determining that the RF energy needs to be blocked on the basis of values received from the plurality of temperature sensors 700. Furthermore, the controller may control the operation of the cooling unit 600 according to a value received from the temperature sensor 700 or the frequency of RF energy currently applied to the tissue.

Figure 2:
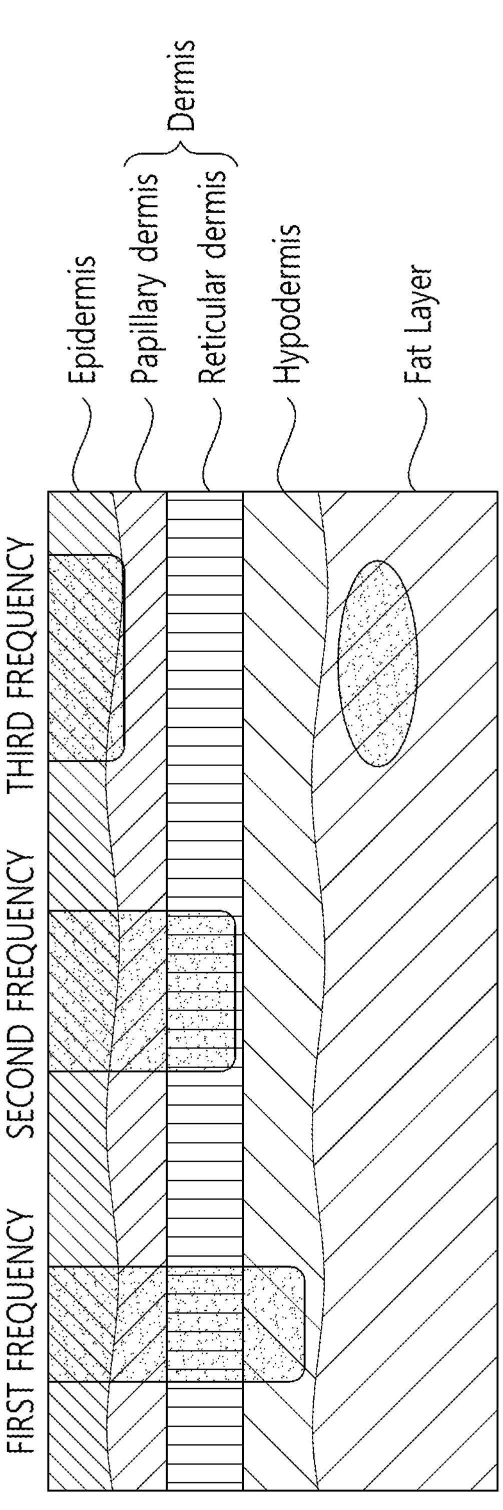
FIG. 2 is a diagram illustrating areas in skin tissue which are heated according to frequencies of RF energy selected in the first embodiment.

FIG. 2 is a diagram illustrating areas in the skin tissue which are heated according to frequencies of RF energy selected in the first embodiment. Here, frequency magnitudes are in the relationship of first frequency<second frequency<third frequency.

Referring to FIG. 2, when RF energy is delivered through the skin, a heating depth may vary depending on the frequency of the RF energy. When the RF electrode is configured as a monopolar electrode, RF energy is delivered from the electrode of the handpiece to a return electrode (not shown) separately attached to the human body. It has been revealed that a heated area within skin tissue varies depending on the frequency of RF energy.

Skin tissue can be divided into epidermis, dermis (papillary dermis and reticular dermis), hypodermis, and fat layer from the surface. Layers constituting the skin tissue may have different conductivities and dielectric constants for RF frequencies. By adjusting the frequency of RF energy using such electrical characteristics of the tissues, it is possible to heat the skin to a desired heating depth.

In the present disclosure, a heated area within the skin tissue can be controlled by adjusting the frequency of RF energy such that the skin treatment device can achieve optimal treatment effect.

As the frequency of RF energy increases within a certain range, the tissue is heated to a shallower depth. The controller can control a heated area within the tissue by adjusting the frequency of RF energy to the first frequency, second frequency, and third frequency. The first frequency may be selected as a frequency capable of heating the skin tissue from the epidermis to the dermis and hypodermis. The second frequency may be selected as a frequency capable of heating the skin tissue from the epidermis to the dermis. The third frequency may be selected as a frequency capable of selectively heating the deep fat layer. Here, the RF energy at the third frequency can heat the superficial portion and deep fat cells of the skin tissue. As described above, it is possible to selectively heat the deep fat layer by applying RF energy having a specific frequency according to the electrical characteristics of each layer of the skin tissue.

The first frequency may be in the range of 1 to 3 MHz, the second frequency may be in the range of 3 to 10 MHz, and the third frequency may be in the range of 10 to 30 MHz. As a more specific example, the first frequency may be 2 MHz, the second frequency may be 6 MHz, and the third frequency may be 13 MHz. As an example, the first frequency may be 2.26 MHz, the second frequency may be 6.75 MHz, and the third frequency may be 13.56 MHz.

However, the present disclosure is not limited to the frequencies described above, and in the present disclosure, the first frequency, second frequency, and third frequency can be defined as frequency regions by which a heating depth within the tissue varies, and the third frequency can be selected as a frequency range that can heat fat cells better than other layers constituting the skin.

Figure 3:
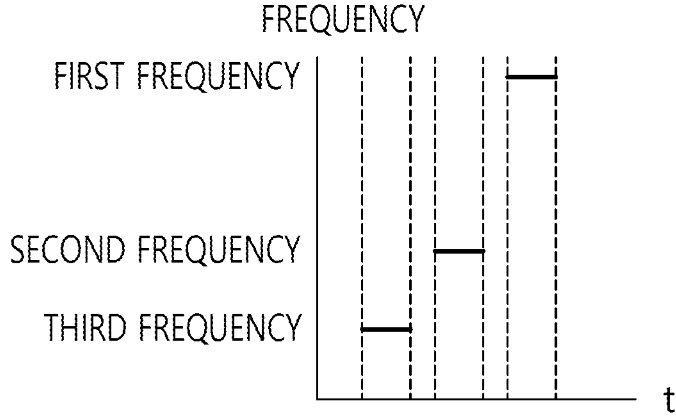
FIG. 3 is a diagram illustrating an example of a pulse train of RF energy in the first embodiment.

FIG. 3 is a diagram illustrating an example of a pulse train of RF energy in the first embodiment.

Referring to FIG. 3, in the first embodiment, the pulse train of RF energy may be composed of, for example, a first frequency of 1 to 3 MHz, a second frequency of 3 to 10 MHz, and a third frequency of 10 to 30 MHz.

Meanwhile, when RF energy is delivered within the skin tissue, the difference in energy delivery efficiency depending on temperature may change rapidly. This is caused by changes in impedance within the tissue depending on temperature differences. Therefore, at the time of delivering RF energy to treat deep tissue, the RF energy delivery efficiency can be improved if preheating is performed in the direction in which the RF energy is delivered.

Meanwhile, as an example of a frequency constituting a pulse train in the present disclosure, the first frequency for initially heating the epidermis, dermis, and hypodermis layers is set to 2.26 MHz. Thereafter, a predetermined rest period is provided in the pulse train, and then 6.75 MHz is selected as the second frequency for heating the epidermal layer and dermis. If the RF energy of the second frequency is delivered in a state in which the epidermis, dermis, and hypodermis layers have been heated by the RF energy of the first frequency, the efficiency of RF energy delivery to the dermis layer can be maximized. Thereafter, a predetermined rest period is provided in the pulse train, and then the third frequency for heating the fat layer may be set to 13.56 MHz. Here, since the RF energy at the first frequency and the RF energy at the second frequency have already been delivered and thus the epidermal layer and dermal layer have been heated, the electrical characteristics of each layer of the tissue change and the heat distribution pattern within the tissue changes. Finally, when the RF energy at the third frequency for heating the fat layer is applied to the skin tissue, the RF energy delivery efficiency is increased, and selective heating of the fat layer is efficiently achieved. Further, from a thermal perspective, the fat layer is heated in a state in which the hypodermis has been heated in advance, and thus heat loss from the heated fat layer to the surface can be minimized.

However, the aforementioned predetermined rest periods may be omitted. Additionally, in a case where a plurality of electrodes is configured, RF energy of different frequencies may be delivered to the electrodes. In this case, RF energy of at least two of the first frequency, second frequency, or third frequency may be overlapped and delivered to the tissue.

As described above, the present disclosure uses multi-frequency RF energy to maximize the RF energy delivery efficiency depending on heating depth. In addition, tissue adjacent to fat cells is heated according to the pulse pattern of the basic pulse train, and the frequencies of pulses of RF energy are adjusted such that the deep tissue can be heated.

Figure 4:
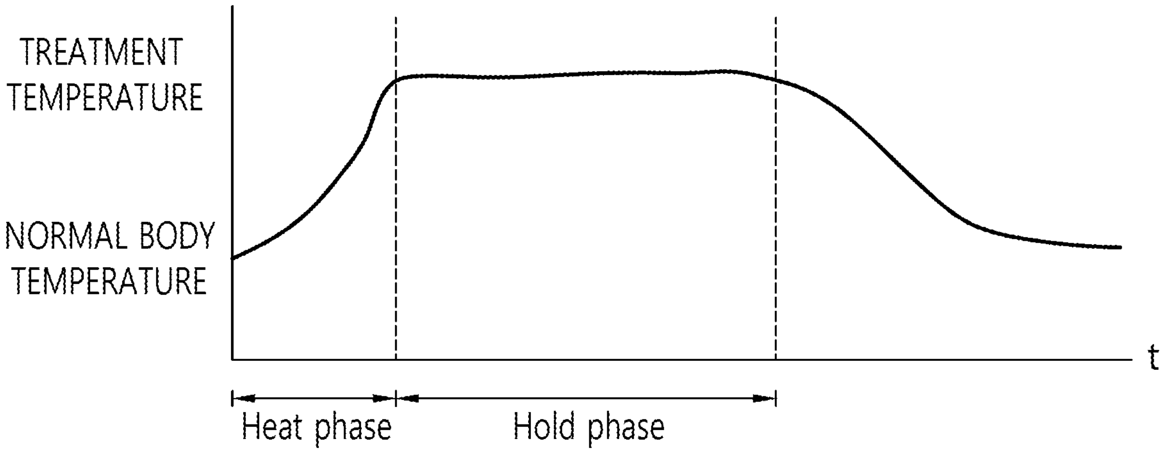
FIG. 4 is a graph showing a heat phase and a hold phase according to the temperature of the tissue when RF energy is delivered in the first embodiment.

FIG. 4 is a graph showing a heat phase and a hold phase according to the temperature of tissue when RF energy is delivered in the first embodiment.

Referring to FIG. 4, when delivering RF energy to kill fat cells, a treatment interval can be distinguished according to the temperature of the fat layer. The treatment interval may be divided into a heat phase, which is an interval in which RF energy is delivered to the fat layer to heat the same, and a hold phase, which is an interval in which the fat layer is maintained at a treatment temperature. The controller may configure different pulse trains for the heat phase and the hold phase. As an example, the frequency of the first frequency may be adjusted differently or the frequency of the third frequency may be configured differently in the respective phases. As another example, pulse trains may be configured with different ratios of the first frequency: second frequency: third frequency in the heat phase and the hold phase. As an example, a pulse train may be configured with a ratio of the first frequency: second frequency: third frequency of 2:3:5 in the heat phase, and a pulse train may be configured with a ratio of 1:3:6 in the hold phase.

Additionally, at least one of pulse widths constituting a pulse train may be adjusted. That is, the pulse width of the first frequency can be increased in the heat phase, and the pulse width of the third frequency can be increased in the hold phase.

Figure 5:
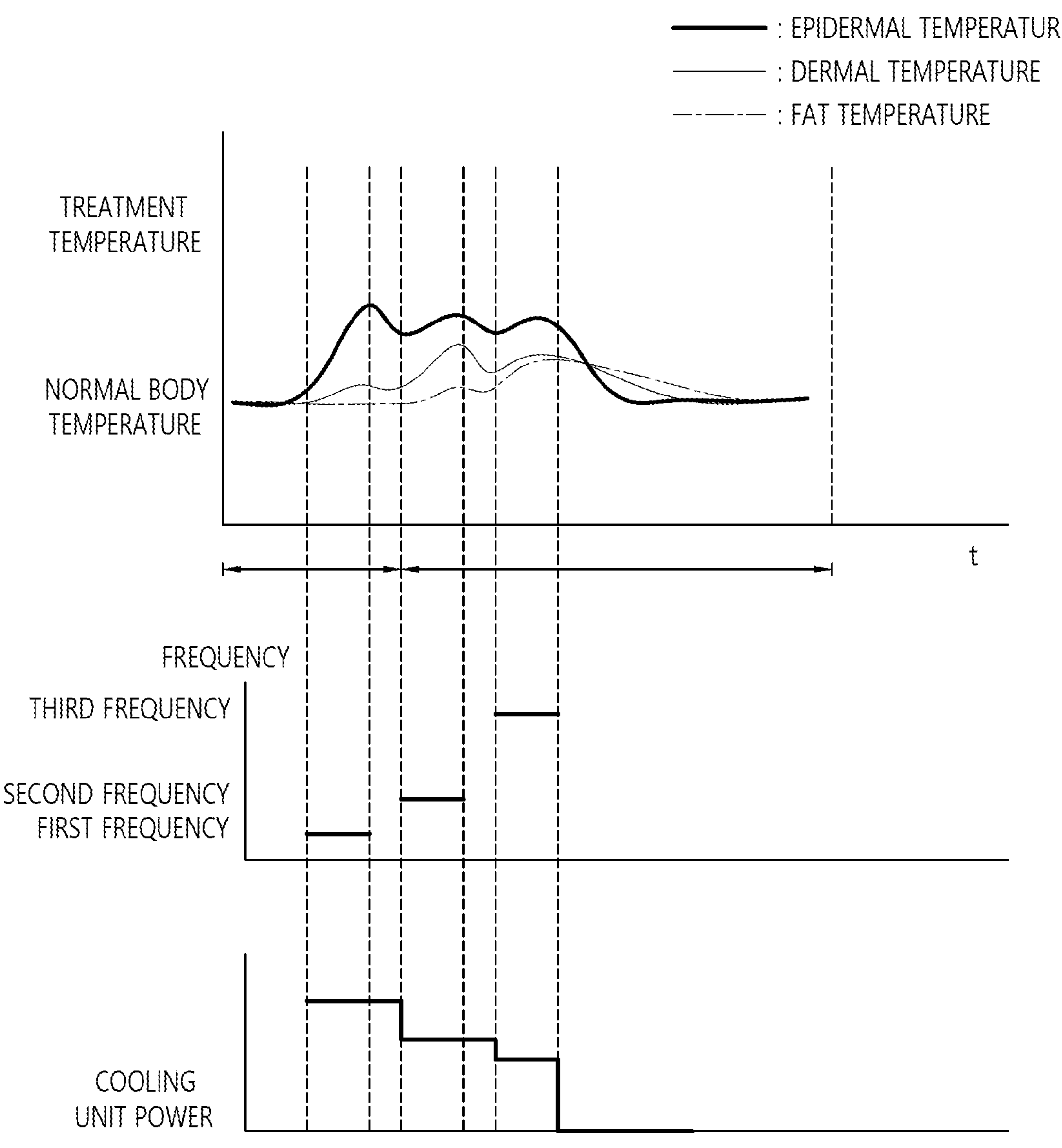
FIG. 5 is a diagram showing a pulse train of RF energy, a tissue temperature, and operation time of a cooling unit in the first embodiment.

FIG. 5 is a diagram showing a pulse train of RF energy, a tissue temperature, and operation time of the cooling unit in the first embodiment.

For skin remodeling, it is necessary to heat the dermis layer to a temperature at which the dermis layer can be denatured, for example, 70° C. to 80° C., to denature the dermis layer into a coagulation state.

Meanwhile, change in the curvature of the skin surface acts as a major factor of change in the face shape. Curvature of the skin surface can be corrected by changing the thickness of the fat layer present in the deep area in the tissue. The death of fat cells prevents additional accumulation of fat and ultimately has the effect of thinning the fat layer. It is known that heating to 44° C. to 46° C. is necessary to kill fat cells.

In the case of treating the dermis and fat of the skin simultaneously, it is necessary to denature the dermis layer and kill fat cells present in the fat layer simultaneously for skin remodeling.

If a pulse train is determined in the order of 2.26 MHz, 6.75 MHz, and 13.56 MHz, the epidermis, dermis, and hypodermis are heated first, and finally the fat layer can be heated to a treatment temperature. Here, since the temperature of the epidermal layer may continuously increase, the epidermal layer may be cooled to prevent excessive damage.

The controller can adjust the power of the cooling unit on the basis of the frequencies constituting the pulse train. The controller can increase the power of the cooling unit when RF energy is delivered at a frequency of 2.26 MHz, used to heat the epidermis to the hypodermis. On the other hand, the controller can decrease the power of the cooling unit when RF energy is delivered at a frequency of 13.56 MHz at which the RF energy is concentrated on the deep area.

Figure 6:
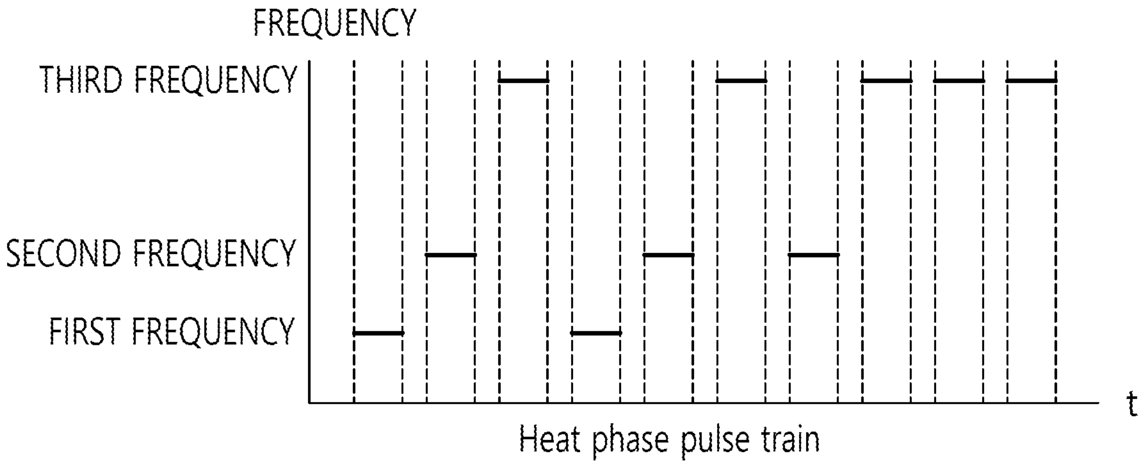
FIG. 6 is a diagram showing a heat phase pulse train in the first embodiment.
Figure 7:
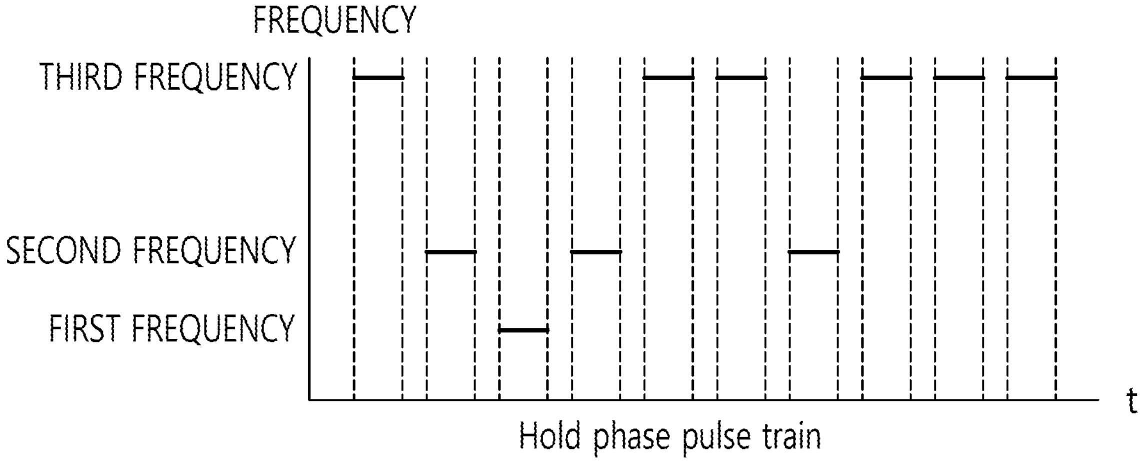
FIG. 7 is a diagram showing a hold phase pulse train in the first embodiment.

FIG. 6 is a diagram showing a heat phase pulse train in the first embodiment, and FIG. 7 is a diagram showing a hold phase pulse train in the first embodiment.

In the present disclosure, the controller may configure different pulse trains for the heat phase and the hold phase.

As an example, referring to FIG. 6, the controller may set the ratio of the first frequency: second frequency: third frequency included in the pulse train to 2:3:5 in order to rapidly heat the tissue to a treatment temperature in the heat phase. Here, when applying RF energy to the tissue for the first time, it is preferable to configure the pulse train in the order of the first frequency for heating the epidermis, dermis, and hypodermis, and the second frequency for heating the epidermis and dermis. The process of delivering RF energy in the order of the first frequency, second frequency, and third frequency may be repeated a predetermined number of times within the heat phase.

As another example, referring to FIG. 7, the controller may determine the ratio of the first frequency: second frequency: third frequency included in the pulse train as 1:3:6 in the hold phase to prevent damage while maintaining the tissue at the treatment temperature. That is, the frequency of the third frequency for delivering RF energy to the fat layer with the highest specific heat after the temperature of the tissue is raised to the treatment temperature can be set to the highest. The frequency of the third frequency in the pulse train in the hold phase may be set to be higher than the frequency of the third frequency in the heat phase. In the temperature hold phase, the frequency of the third frequency for selectively heating fat cells is increased to maintain fat cells with a high specific heat at the treatment temperature. Further, pulses adjusted to the second frequency and the first frequency may be applied to the tissue to maintain the epidermal layer and dermal layer at the treatment temperature in the hold phase.

After a predetermined time has elapsed, the controller may stop delivering RF energy. The ratios of frequencies of the pulse trains described above are merely examples, and the controller may configure pulse trains with different frequencies of frequencies in the heat phase and the hold phase.

Figure 8:
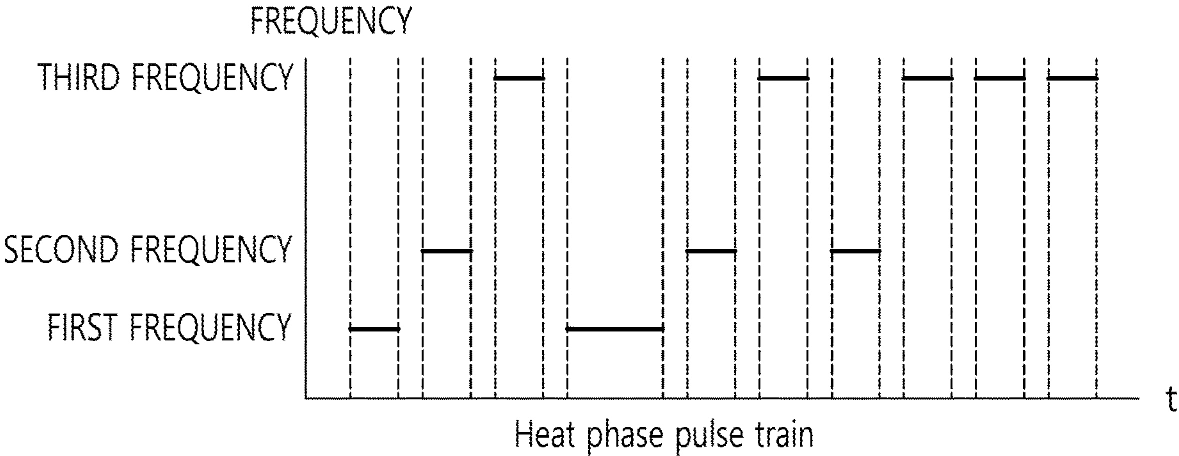
FIGS. 8 and 9 are diagrams showing pulse trains with adjusted heat phase pulse widths in the first embodiment.
Figure 9:
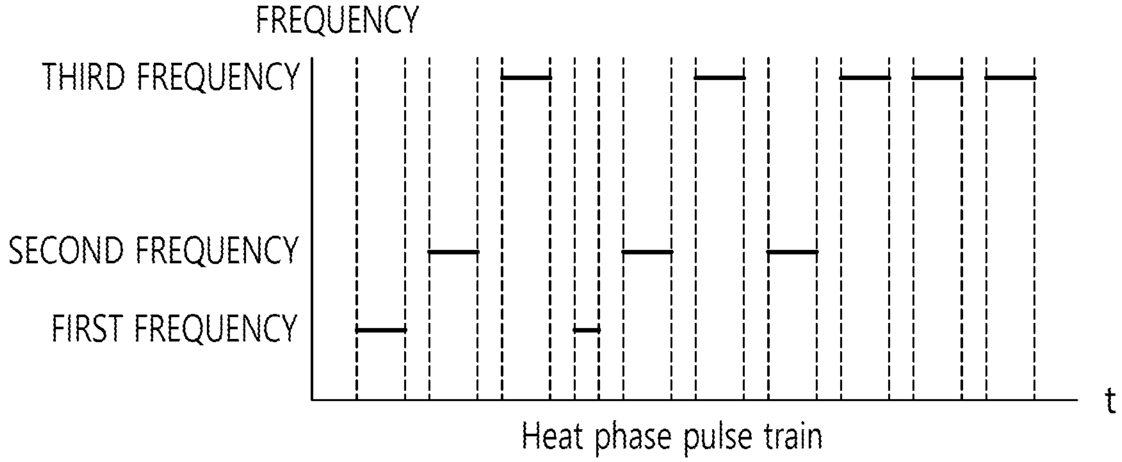

FIGS. 8 and 9 are diagrams showing pulse trains with adjusted heat phase pulse widths in the first embodiment.

The controller may adjust pulse widths on the basis of the temperature of the tissue measured during transmission of RF energy.

Referring to FIG. 8, when delivering RF energy while adjusting the frequency according to the pulse train in the heat phase, the controller can increase the pulse width of the first frequency (2.26 MHz) such that the temperature of the skin surface can increase in a case where a measured temperature of the skin surface is lower than a required temperature.

Referring to FIG. 9, contrary to FIG. 8, in a case where a measured temperature of the skin surface is higher than the required temperature, the controller can prevent excessive temperature increase in the epidermis by reducing the pulse width of the first frequency.

Although FIGS. 6 to 9 show pulse trains in which the frequencies of RF energy pulses are adjusted, the present disclosure can be modified and applied in such a manner that RF energy is adjusted to each frequency and delivered to the tissue as a single pulse.

Hereinafter, a method of controlling a skin treatment device for denaturing tissue using multi-frequency RF energy according to a second embodiment of the present disclosure will be described with reference to FIGS. 10 and 11.

Figure 10:
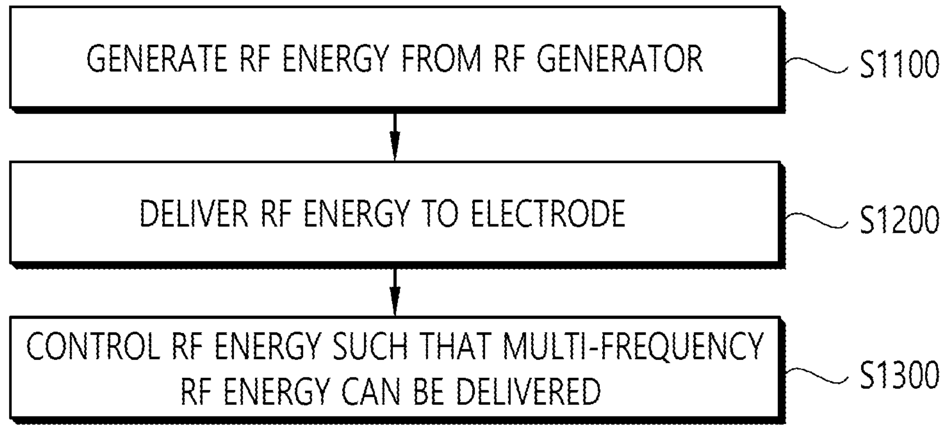
FIG. 10 is a flowchart of a method of controlling a skin treatment device for denaturing tissue using multi-frequency RF energy according to a second embodiment of the present disclosure.

FIG. 10 is a flowchart of the method of controlling a skin treatment device for denaturing tissue using multi-frequency RF energy according to a second embodiment of the present disclosure.

Referring to FIG. 10, the method of controlling a skin treatment device for denaturing tissue using multi-frequency RF energy according to the second embodiment of the present disclosure includes a step S1100 of generating RF energy from an RF generator, a step S1200 of delivering the RF energy to an electrode, and a step S1300 of controlling the RF energy such that multi-frequency RF energy can be delivered.

The step S1100 of generating RF energy from the RF generator corresponds to a step of generating RF energy when certain requirements are met according to user input or by a predetermined algorithm. This step can be performed through a controller controlling the RF generator. Here, conditions determined by the controller may be whether the electrode maintains contact with the tissue based on values measured from the electrode.

The step S1200 of delivering the RF energy to the electrode corresponds to a step of delivering the RF energy to the electrode.

The step S1300 of controlling the RF energy such that multi-frequency RF energy can be delivered corresponds to a step of adjusting the frequency and/or pulse width of the RF energy delivered to the electrode. This step may include a step in which the controller controls the RF modulator to adjust the frequency of the RF energy. The controller can adjust the frequency of the RF energy to at least three frequencies for heating different areas in the tissue.

The controller may control the RF energy according to a predetermined pulse train. As an example, first, the controller determines frequencies of a first frequency (2.26 MHz) for heating the epidermis, dermis, and hypodermis, a second frequency (6.75 MHz) for heating the dermis layer, and a third frequency (13.56 MHz) for selectively heating fat and configure a pulse train.

The controller may adjust the frequencies and/or pulse widths of the first to third frequencies constituting the pulse train as treatment time elapses and the temperature of the skin surface increases. The controller may adjust the frequency/pulse width of each frequency in real time. Thereafter, the control unit may perform control such that RF energy is blocked under predetermined conditions, for example, on the basis of the total amount of RF energy delivered or when the treatment time has elapsed.

Although not shown, the controller may adjust the power of the cooling unit to cool the skin surface based on the temperature of the tissue surface and/or the frequency of the applied RF energy.

Figure 11:
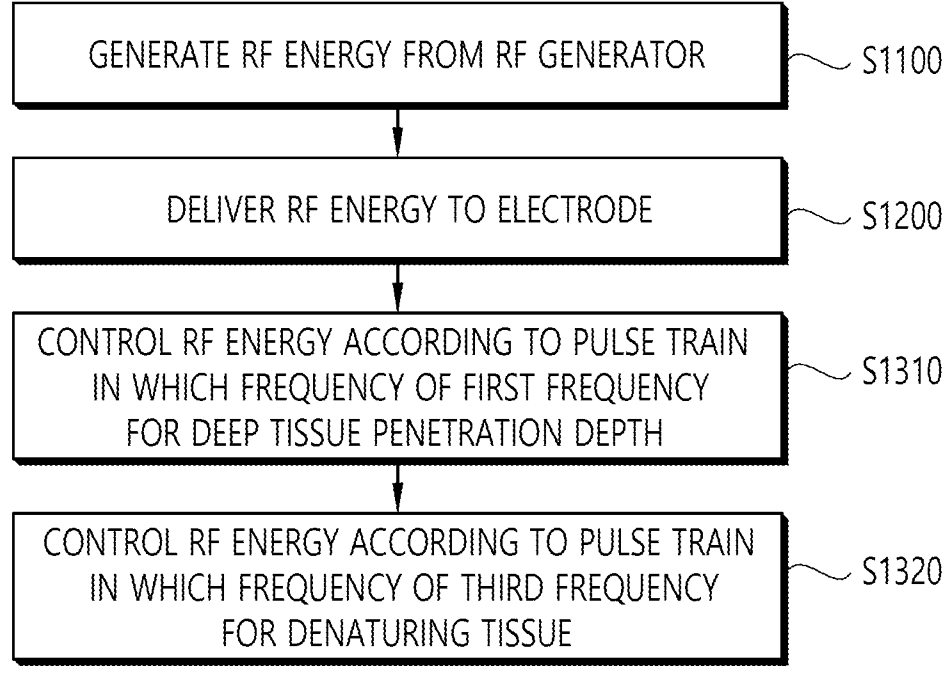
FIG. 11 is a detailed flowchart of the second embodiment of the present disclosure.

FIG. 11 is a detailed flowchart of the second embodiment of the present disclosure.

Referring to FIG. 11, in the second embodiment, the step S1300 of controlling the RF energy such that multi-frequency RF energy can be delivered may include a heat phase control step S1310 of controlling the RF energy according to a pulse train in which the frequency of the first frequency for heating a deep portion in the tissue is high, and a hold phase control step S1320 of controlling the RF energy according to a pulse train in which the frequency of the third frequency for denaturing tissue is high.

The heat phase control step S1310 of controlling the RF energy according to a pulse train in which the frequency of the first frequency for heating a deep area in the skin tissue is high is performed to rapidly heat the tissue to a treatment temperature in the initial stage. At this time, if the temperatures of the epidermis, dermis, and hypodermis increase to a certain temperature or higher, the efficiency of RF energy delivery to the deep fat layer increases. Therefore, the controller increases the frequency of the first frequency such that the temperatures of the epidermis layer, dermis layer, hypodermis, and fat layer can rapidly increase to treatment temperatures thereof. Here, the frequency of the first frequency in this step S1310 may be higher than that in the step S1320 which will be described later.

Hold phase control step S1320 involves controlling RF energy according to a pulse train where the frequency of the third frequency for tissue denaturation is high corresponds to a step of controlling the RF energy to maintain the tissue at a treatment temperature. The controller may perform control for maintaining the treatment temperature of fat layer, which has a higher specific heat than the epidermal layer or dermal layer and thus has a slow temperature increase, at the treatment temperature. As an example, the controller may control RF energy by increasing the frequency of selecting 13.56 MHz as the third frequency capable of selectively heating the fat layer. Here, selective heating of the fat layer means that the fat layer is heated because the RF energy absorption rate in fat is higher than that in other layers of the skin tissue when RF energy is delivered at the third frequency.

Consequently, the controller can adjust the frequency of selecting a frequency from among multiple frequencies of RF energy at the beginning and end of RF energy transmission such that optimal treatment can be performed.

The method of controlling a skin treatment device for denaturing tissue using multi-frequency RF energy described above with reference to FIGS. 10 and 11 is applicable to the skin treatment device for denaturing tissue using multi-frequency RF energy according to the first embodiment of the present disclosure described with reference to FIGS. 1 to 9.

Figure 12:
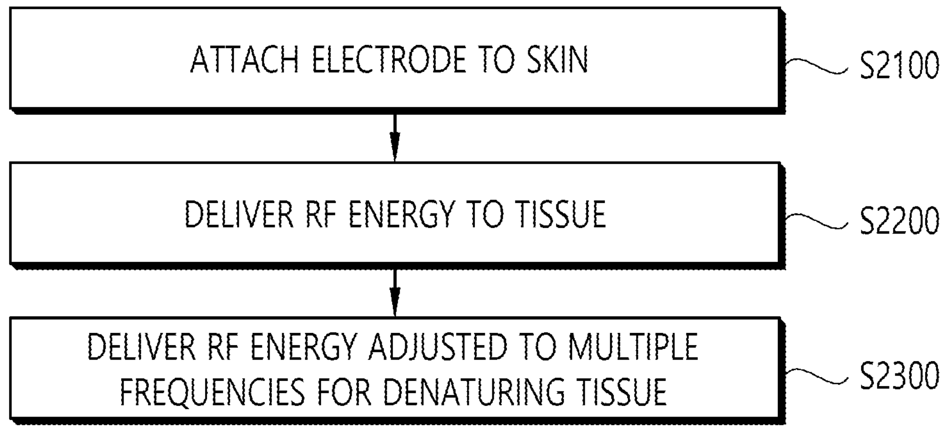
FIG. 12 is a flowchart of a treatment method for denaturing tissue using multi frequency RF energy, which is a third embodiment of the present disclosure.

FIG. 12 is a flowchart of a treatment method for denaturing tissue using multi frequency RF energy, which is a third embodiment of the present disclosure.

Referring to FIG. 12, the treatment method for denaturing tissue according to the third embodiment of the present disclosure may include a step S2100 of attaching an electrode to the skin, a step S2200 of delivering RF energy to the tissue, and a step S2300 of adjusting the RF energy adjusted to multiple frequencies for denaturing tissue.

The step S2100 of attaching the electrode to the skin corresponds to a step of attaching the electrode to the tissue determined by a user to require treatment in the patient's skin. The user (or medical staff) selects an area deemed necessary to change the face shape and attaches the electrode capable of delivering RF energy to the skin.

The step S2200 of delivering RF energy to the tissue corresponds to a step of delivering the RF energy to the tissue by user operation in a state in which the electrode is in close contact with the skin.

The step S2300 of delivering the RF energy adjusted to multiple frequencies for denaturing tissue corresponds to a step of controlling heated areas at different depths in the tissue by adjusting the frequency of the RF energy. Skin tissue includes the epidermis, dermis, hypodermis, and fat layer, and the respective layers require different temperatures for treatment. The epidermal layer and dermal layer are degenerated for tissue remodeling, and at this time, the temperature of the tissue for degeneration may be 70° C. to 80° C. Fat treatment can be performed by heating the fat layer to 44° C. to 46° C. and maintaining the same for a predetermined time to kill the fat cells. This step S2300 is performed to prevent excessive damage to the epidermis and dermis layers and to maintain the fat layer at the treatment temperature. In this step, the multiple frequencies may include the first frequency for heating the epidermis, dermis and hypodermis, the second frequency for heating the dermis layer, and the third frequency for selectively heating fat. In this step, the frequencies of the first frequency, second frequency, and third frequency may vary depending on the treatment mode.

That is, in this step, heating of the epidermis, dermis, and hypodermis is performed at a higher frequency in an early treatment mode, and the frequency of heating the epidermis, dermis, and hypodermis can be lowered in a later treatment mode. Additionally, the frequency of heating the fat layer can be lowered at the beginning of treatment and then increased at the end of treatment.

Further, the third embodiment of the present disclosure may be repeated multiple times to treat the face. That is, the third embodiment of the present disclosure can be performed repeatedly while changing the area to which RF energy is delivered.

Figure 13:
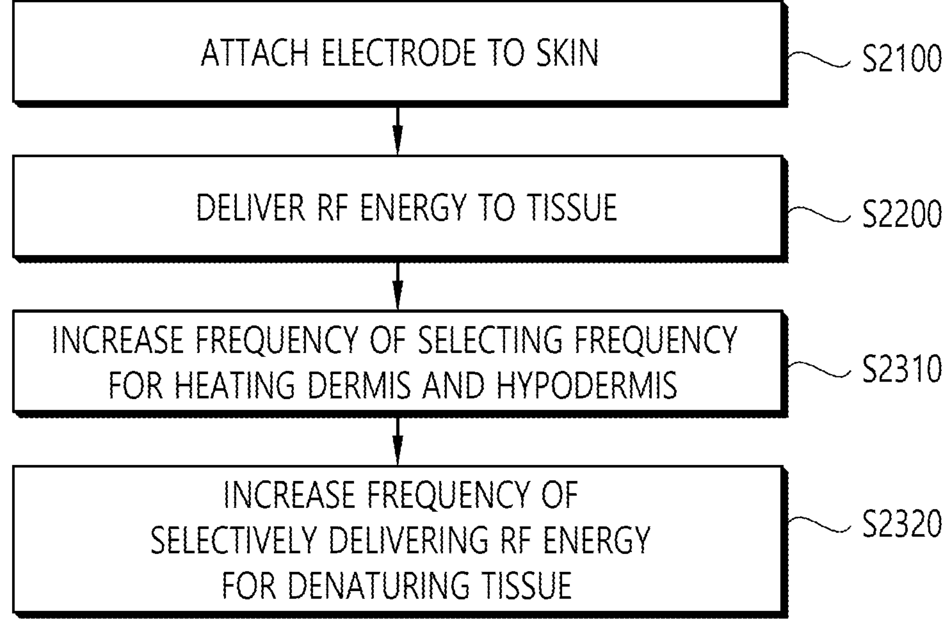

FIG. 13 is a detailed flowchart of the third embodiment.

Referring to FIG. 13, in the third embodiment, the step S2100 of delivering the RF energy to the tissue to treat the fat layer may include a heating step S2310 of increasing the frequency of selecting a frequency for heating a deep area in the tissue, and a holding step S2320 of increasing the frequency of selectively delivering the RF energy to fat cells in the tissue.

The heating step S2310 of increasing the frequency of delivering the RF energy to a deep area in the tissue is a step of rapidly increasing the temperature of the epidermis, dermis, and hypodermis to improve RF energy delivery efficiency according to the pattern in which the RF energy is delivered. At this time, the frequency may be divided into a first frequency region of 1 to 3 MHz, a second frequency region of 3 to 10 MHz, and a third frequency region of 10 to 30 MHz. In this step, the frequency of selecting the frequency of RF energy in the first and second frequency regions may be higher than the frequency of selection in the third frequency region.

The holding step S2320 of increasing the frequency of delivering the RF energy to fat cells in the tissue corresponds to a step of increasing the frequency of the RF energy at the third frequency in order to maintain the temperature of the fat layer at the treatment temperature. At the time of performing this step, RF energy may also be delivered at the first and second frequencies repeatedly to maintain the temperature of the epidermis, dermis, and hypodermis. Meanwhile, the frequency of selecting the third frequency in this step S2320 may be higher than that in the heating step S2310.

The method of denaturing tissue described with reference to FIGS. 12 and 13 may be performed using the skin treatment device for denaturing tissue using multi-frequency RF energy according to the first embodiment of the present disclosure described with reference to FIGS. 1 to 10.

In the following embodiments, the controller may select two frequencies, and deliver the RF energy at the selected frequencies to the tissue. In this case, the frequencies may be divided into a first range, a second range, and a third range according to their magnitudes.

In the following embodiments, the controller may select a first frequency from the first range, the second range or the third range, and select a second frequency from the ranges other than that from which the first frequency is selected. Further, the controller may control the RF source to deliver the RF energy at the selected first frequency to the electrode, and also control the RF source to deliver the RF energy at the second frequency to the electrode.

The term 'RF source' may refer to a configuration capable of generating RF energy at a specific frequency. An RF source can include an RF generator and may incorporate an RF controller.

The frequencies of the RF energy may be modulated by the RF modulator. Alternatively, the operation of one of several RF generators, which can generate RF energy at the frequency of the RF energy, is determined by the selection of one among multiple RF generators.

Figure 14:
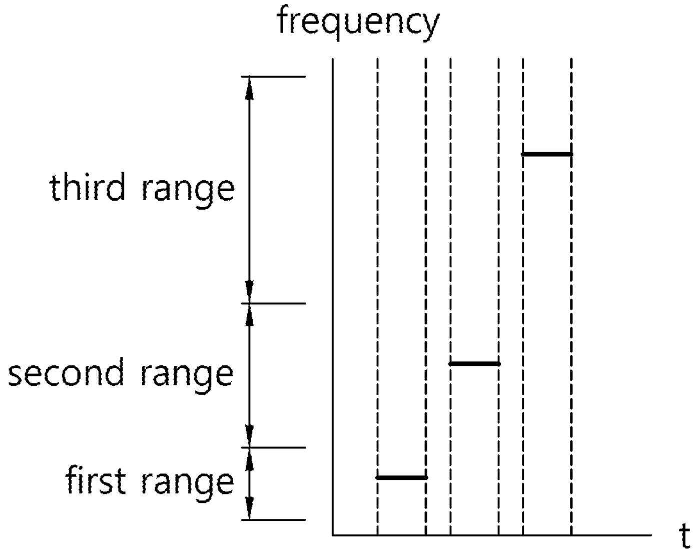
FIG. 14 is a conceptual view showing frequency ranges according to a fourth embodiment of the disclosure.

FIG. 14 is a conceptual view showing frequency ranges according to a fourth embodiment of the disclosure.

Referring to FIG. 14, a treatment apparatus for denaturing tissue with RF energy at multiple frequencies according to the fourth embodiment of the disclosure may generate the RF energy at frequencies adjusted by an RF adjuster into the frequencies selected from the first range, the second range, and the third range.

Here, the frequency ranges, i.e., the first range, the second range, and the third range, for the RF energy may be 1 MHz to 10 GHz.

The frequencies selected in the second range by the RF adjuster may be higher than those in the first range. Likewise, the frequencies in the third range may be higher than those in the second range.

These ranges may be different from one another. For example, the second range may be wider than the first range. Further, the third range may be wider than the second range.

For example, the second range may be 1.1 or more times the first range. Specifically, the second range may be 1.1 to 5 times the first range. Meanwhile, the third range may be twice or more times the second range. Specifically, the third range may be 2 to 10 times the second range.

For instance, the first range may be 1 MHz to 3 MHz, the second range may be 3 MHz to 10 MHz, and the third range may be 10 MHz to 2.45 GHz. In this case, the controller may select 2 MHz as the first frequency and select 6 MHz as the second frequency. Alternatively, the controller may select 2 MHz as the first frequency and select 13 MHz as the second frequency. Alternatively, the controller may select 6 MHz as the first frequency, and select 13 MHz as the second frequency. However, the foregoing selected frequencies are merely examples, and may be selected in the first range, the second range, and the third range.

Figure 15:
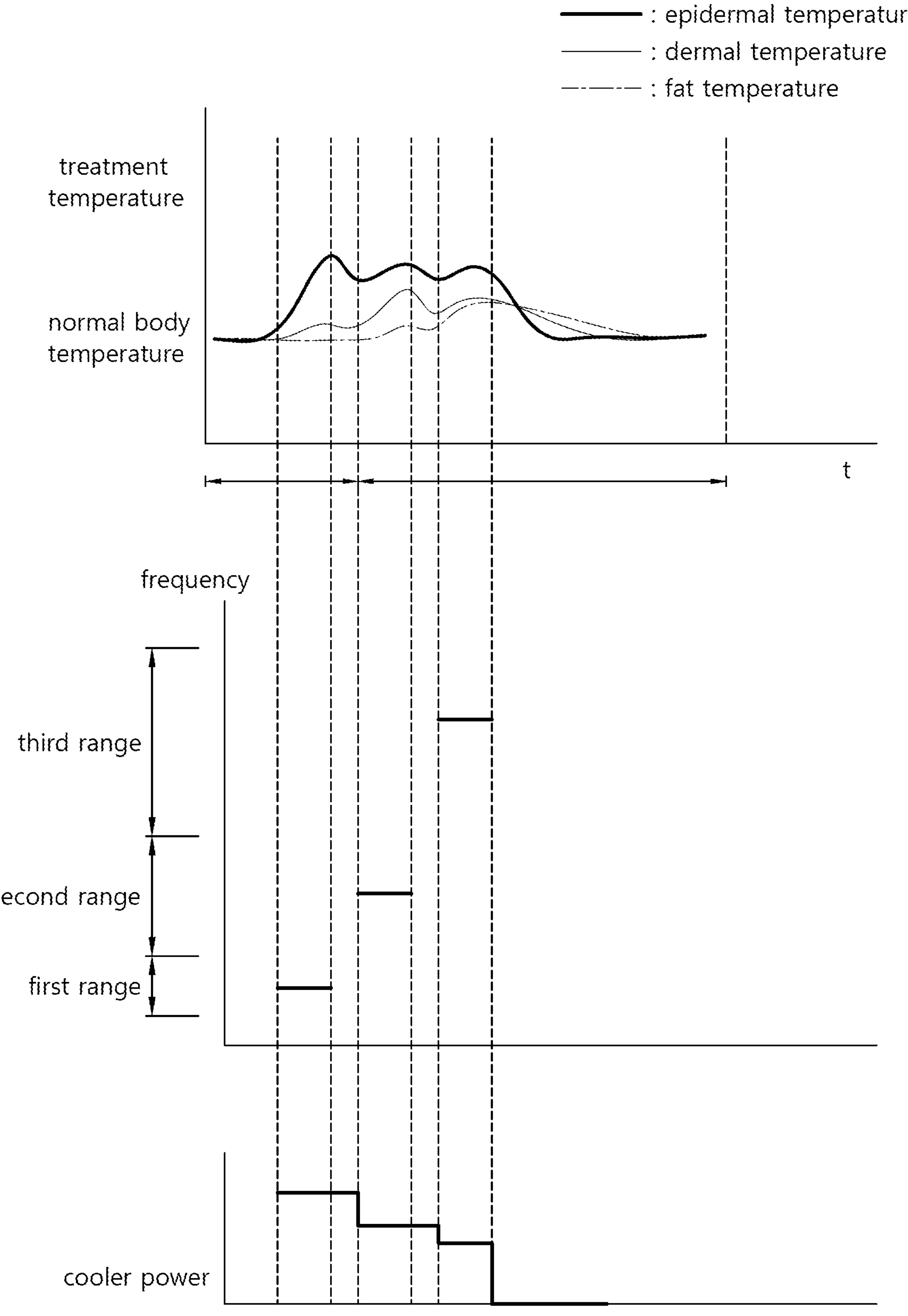
FIG. 15 illustrates a pulse train of RF energy, the temperature of tissue, and an operating time of a cooler according to the fourth embodiment.

FIG. 15 illustrates a pulse train of RF energy, the temperature of tissue, and an operating time of a cooler according to the fourth embodiment.

Referring to FIG. 15, according to the fourth embodiment, the RF energy having a frequency within the first range may exhibit the deepest penetration in skin tissue, and may rapidly increase the temperature of epidermis.

The RF energy having a frequency within the second range may rapidly increase the temperature of dermis.

Figure 16A:
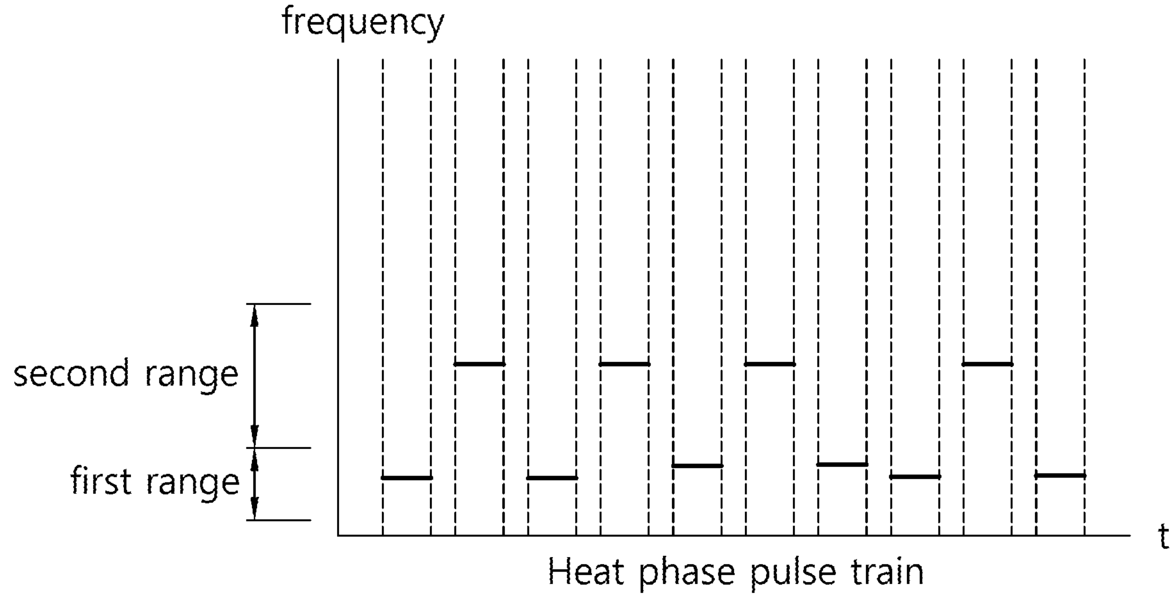
FIGS. 16A, 16B and 16C illustrate the frequencies that make up the pulse trains of the RF energy in the heating phase according to the fourth embodiment.
Figure 16B:
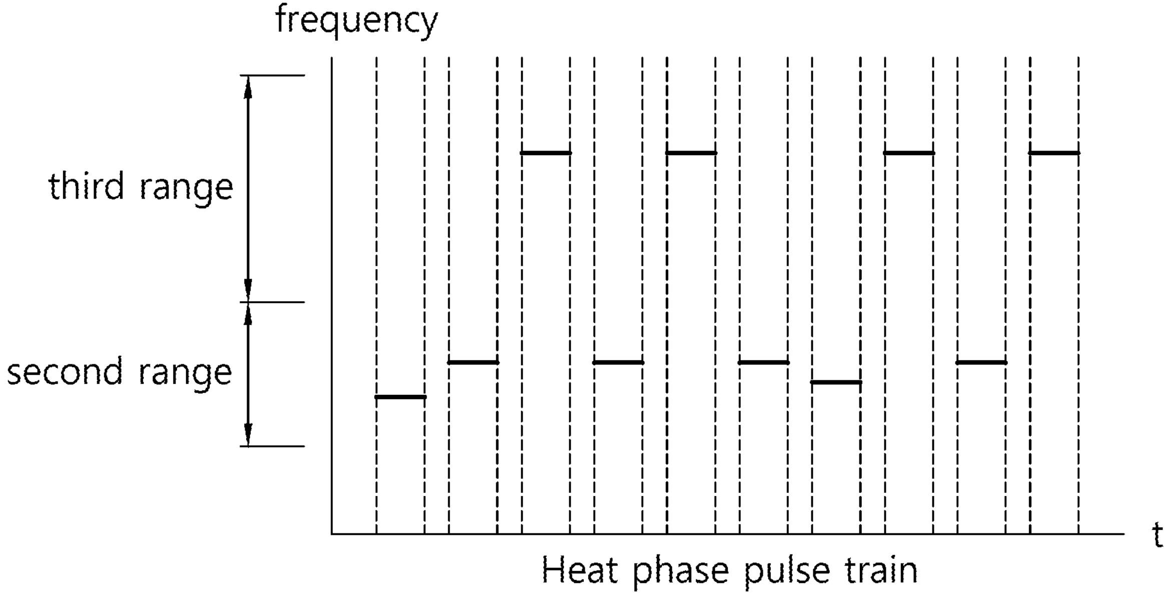
Figure 16C:
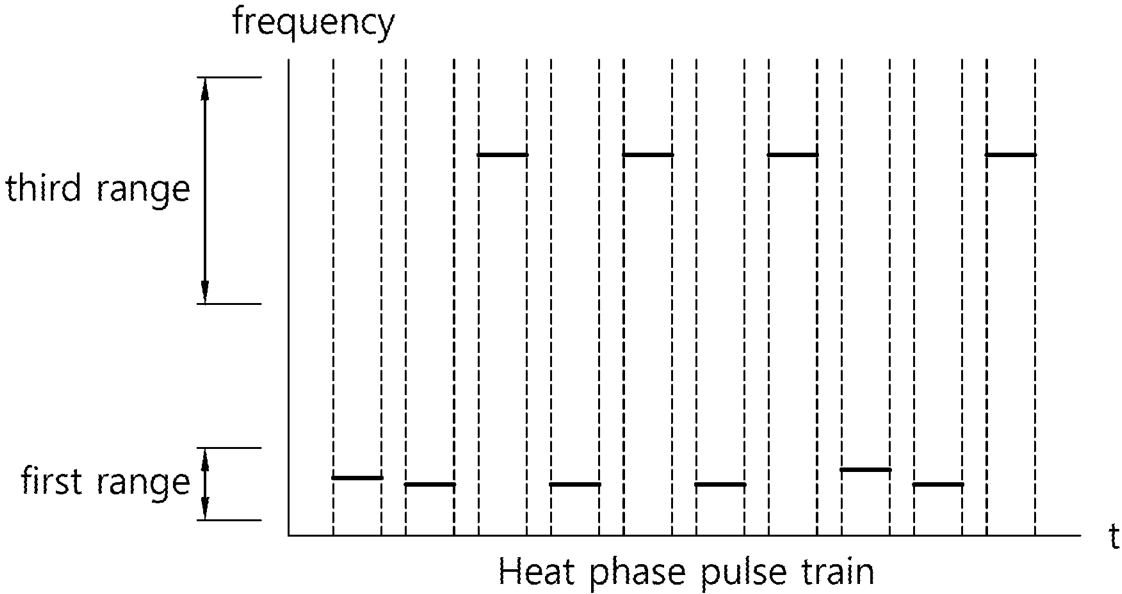

Further, the RF energy having a frequency within the third range may selectively heat the temperature of dermis FIGS. 16A, 16B and 16C illustrate the frequencies that make up the pulse trains of the RF energy in the heating phase according to the fourth embodiment. In this embodiment, the controller may control the RF source to increase the number of times the lower one is selected between the two frequencies in the heating phase.

Referring to FIG. 16A, the controller according to the disclosure may adjust the RF energy by selecting the first frequency from the first range and selecting the second frequency from the second range. Specifically, to raise the temperature of the skin, the number of times the RF energy having the first frequency is applied may be increased.

Referring to FIG. 16B, the controller according to the disclosure may adjust the RF energy by selecting the first frequency from the second range and selecting the second frequency from the third range. Specifically, to heat the epidermis, the number of times the RF energy having the first frequency is applied may be increased.

Referring to FIG. 16C, the controller according to the disclosure may adjust the RF energy by selecting the first frequency from the first range and selecting the second frequency from the third range. Specifically, to raise the temperature of the skin, the number of times the RF energy having the first frequency is applied may be increased.

Meanwhile the controller can vary the control of RF energy frequency selection based on conditions., e.g., the heating phase and the holding phase. In this case, the frequencies are selected from the respective ranges or the frequencies are selected from one range.

Figure 17A:
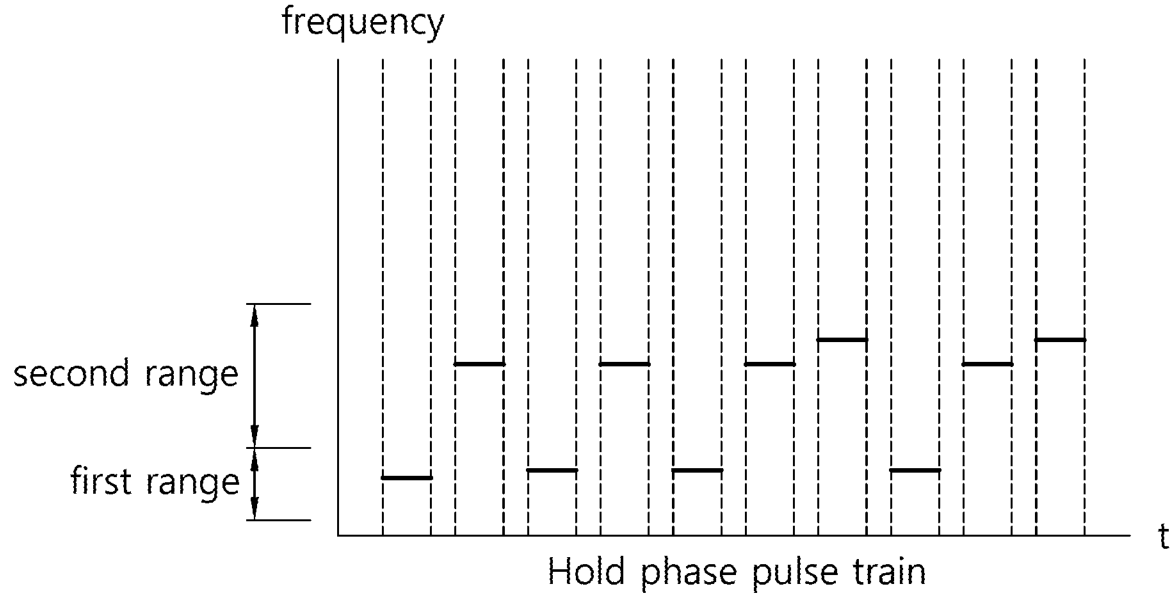
FIGS. 17A, 17B and 17C illustrate the frequencies that make up the pulse trains of the RF energy in the heating phase according to the fourth embodiment.
Figure 17B:
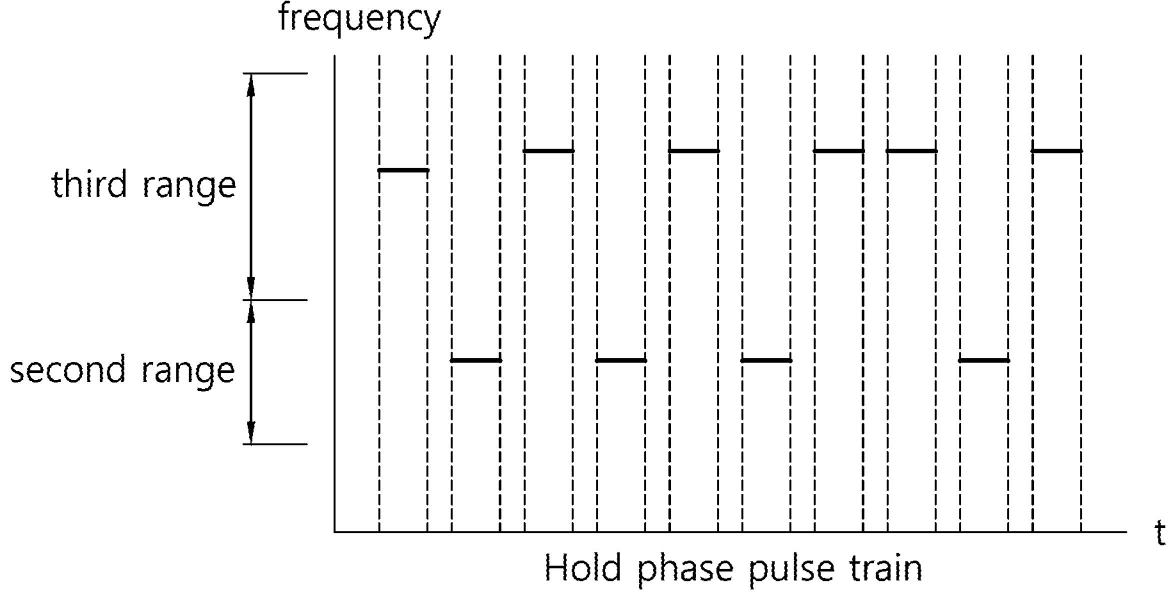
Figure 17C:
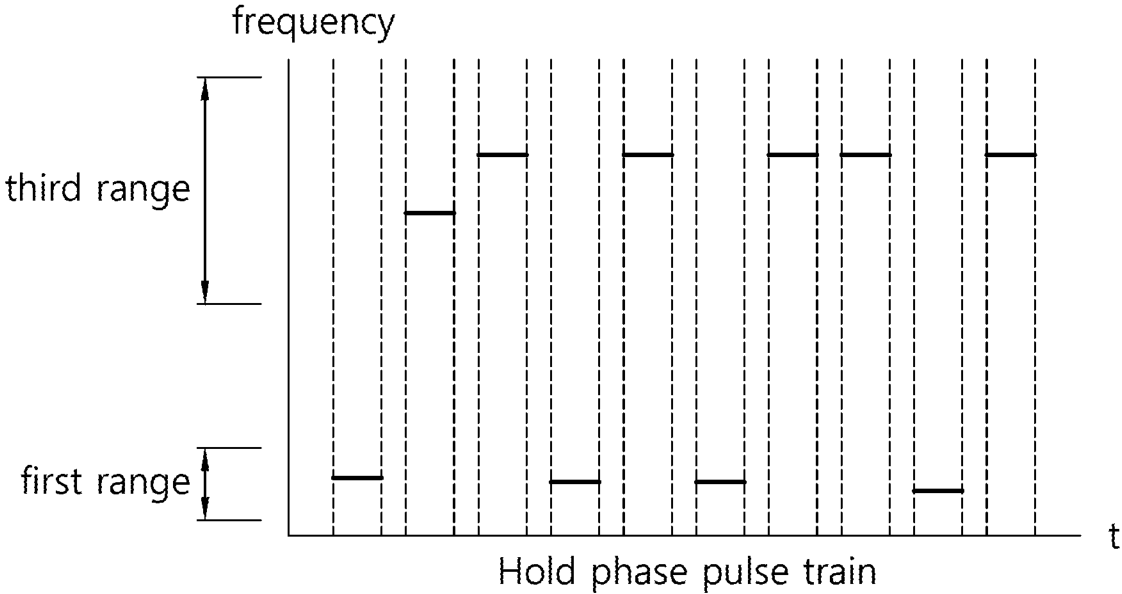

FIGS. 17A, 17B and 17C illustrate the frequencies that make up the pulse trains of the RF energy in the holding phase according to the fourth embodiment. In this embodiment, the controller may control the RF source to increase the number of times the higher one is selected between the two frequencies in the holding phase.

Referring to FIG. 17A, the controller may control the RF source to hold the raised temperature without rapidly raising the temperature of the skin. In this case, the controller may select the first frequency from the first range and select the second frequency from the second range.

Specifically, to hold the temperature of the skin at a predetermined temperature, the controller may control the RF source so that the number of times the RF energy having the second frequency is applied can be increased.

Referring to FIG. 17B, the controller may select the first frequency from the second range and select the second frequency from the third range. Specifically, the controller may increase the number of times the RF energy having the first frequency is applied while holding the temperature of the skin tissue.

Referring to FIG. 17C, controller may select the first frequency from the third range and select the second frequency from the third range. Specifically, the controller may increase the number of times the RF energy having the second frequency is applied while holding the temperature of the skin tissue.

Figure 18A:
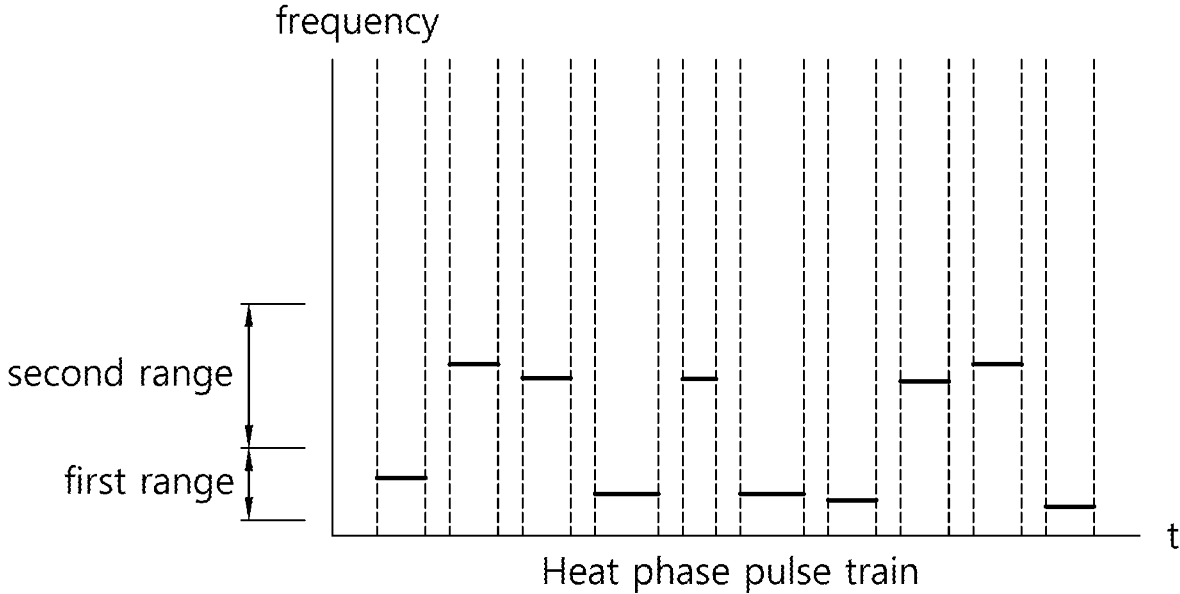
FIGS. 18A, 18B and 18C illustrate alternative examples of the pulse trains of the RF energy in the heating phase according to the fourth embodiment.
Figure 18B:
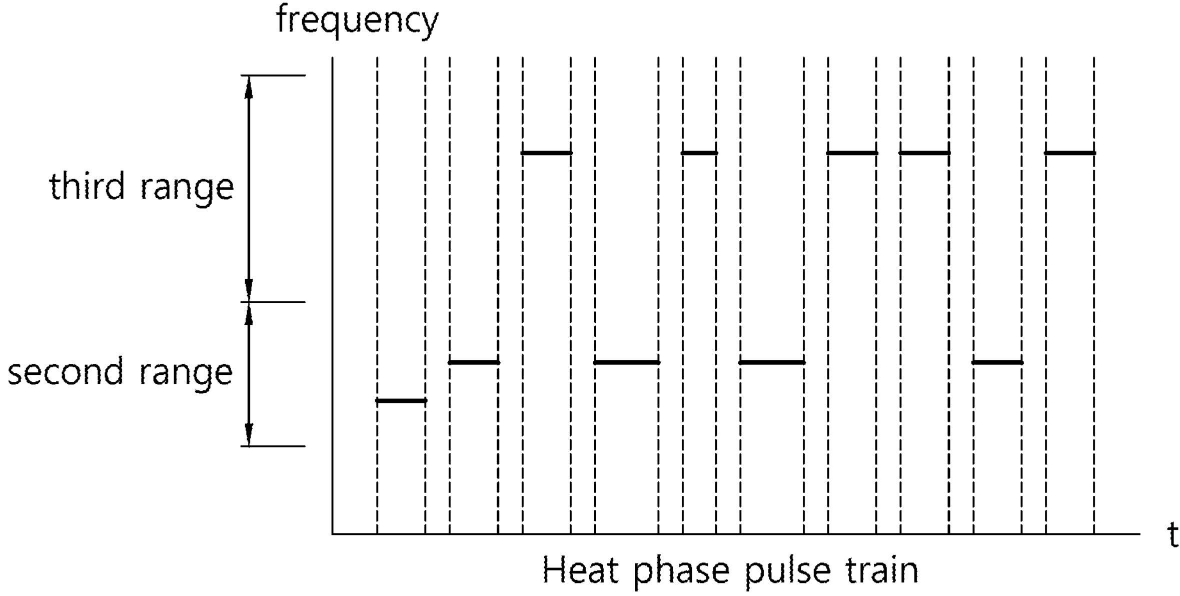
Figure 18C:
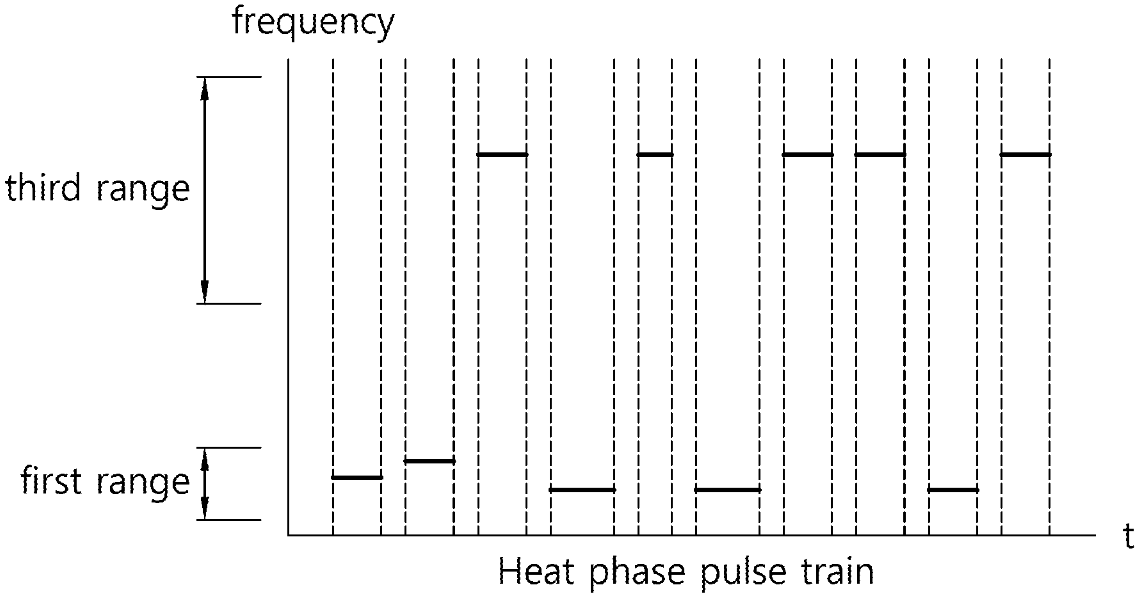

FIGS. 18A, 18B and 18C illustrate alternative examples of the pulse trains of the RF energy in the heating phase according to the fourth embodiment.

Referring to FIGS. 18A, 18B and 18C, according to the fourth embodiment of the disclosure, the controller is configured to adjust the pulse width of the RF energy. The controller selects the first frequency and the second frequency from two ranges in the heating phase, and controls the RF source to generate the RF energy at the selected frequencies.

The controller may increase the pulse width to deliver the RF energy at the frequency selected from a narrow range between the two selected ranges so that heating can be rapidly achieved in the heating phase.

Referring to FIG. 18A, the controller may select the first frequency from the first range and select the second frequency from the second range in the heating phase. Specifically, the controller may control the RF source to make the number of times the RF energy having the first frequency to be similar to the RF energy having the second frequency. However, the controller may increase the pulse width when the RF energy having the first frequency is delivered in the heating phase.

Referring to FIG. 18B, the controller may select the first frequency from the second range and select the second frequency from the third range in the heating phase. Specifically, the controller may control the RF source to make the number of times the RF energy having the first frequency to be similar to the RF energy having the second frequency. However, the controller may increase the pulse width when the RF energy having the first frequency is delivered in the heating phase.

Referring to FIG. 18C, the controller may select the first frequency from the first range and select the second frequency from the third range in the heating phase. Specifically, the controller may control the RF source to make the number of times the RF energy having the first frequency to be similar to the number of times the RF energy having the second frequency. However, the controller may control the number of times the frequency selected from first range to be similar to the number of times selected from the third range in the heating phase. However, the controller may increase the pulse width when the RF energy having the first frequency is delivered in the heating phase.

Figure 19:
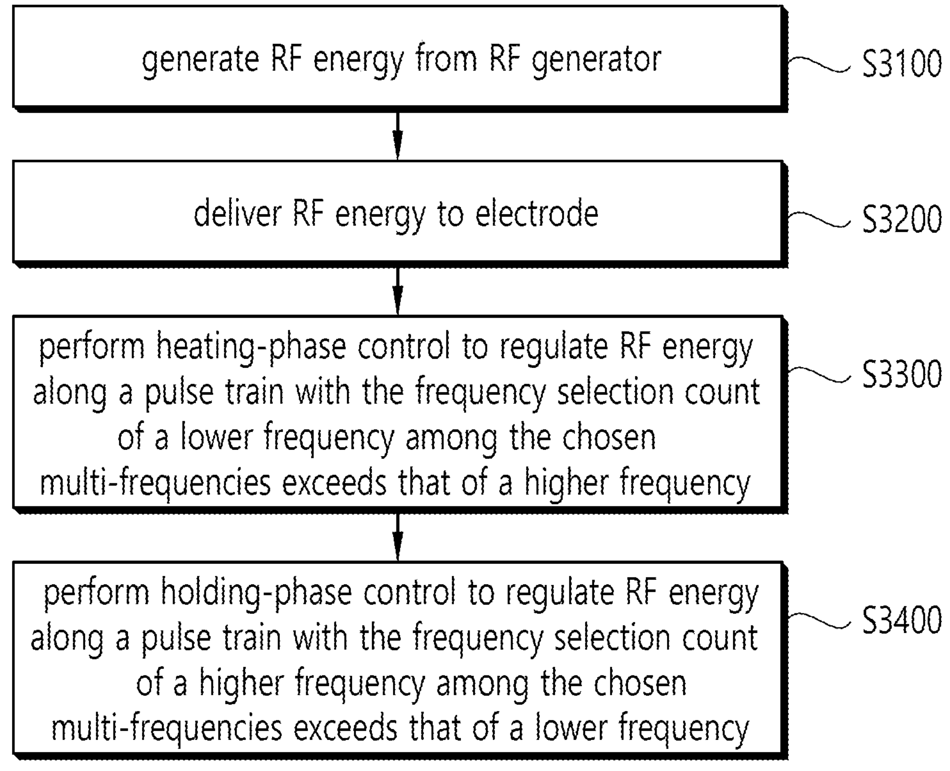
FIG. 19 is a flowchart showing a control method of the treatment apparatus for denaturing tissue with RF energy having multiple frequencies according to a fifth embodiment of the disclosure.

FIG. 19 is a flowchart showing a control method of the treatment apparatus for denaturing tissue with RF energy having multiple frequencies according to a fifth embodiment of the disclosure.

Referring to FIG. 19, the control method of the treatment apparatus for denaturing tissue with RF energy having multiple frequencies according to the fifth embodiment of the disclosure may include steps of generating the RF energy (S3100), delivering the RF energy to an electrode (S3200), controlling the RF energy in a heating phase (S3300), and controlling the RF energy in a holding phase (S3400).

The step S3100 of generating the RF energy and the step S3200 of delivering the RF energy to the electrode may be performed as described above in the second embodiment.

In this embodiment, the step S3300 of controlling the RF energy during the heating phase includes adjusting the RF energy along the pulse train, there are more pulses of a low frequency among the multiple frequencies. The multiple frequencies may be selected within the first range, the second range or the third range.

In the step S3300 of controlling the RF energy in the heating phase, the multiple frequencies may be selected from two ranges. In this step S3300, the RF energy may be delivered having a frequency changed into frequencies selected from two different ranges. In this case, the controller may select the first frequency from the first range, and select the second frequency from the second range. The controller may control the RF source to generate the RF energy at the first frequency and then generate the RF energy at the second frequency.

Further, the controller may select the first frequency within the first range and select the second frequency within the third range, or may select the first frequency within the second range and select the third frequency within the third range.

Further, the controller may select the first frequency within the third range and select the second frequency within the second range, or may select the first frequency within the second range and select the second frequency within the first range, or may select the first frequency within the third range or select the second frequency within the first range.

Further, according to the fifth embodiment, the pulse train is configured for the frequencies so that the RF energy can be delivered at the first and second frequencies selected from the respective ranges, thereby controlling the RF energy based on the pulse train.

In the step S3300 of controlling the RF energy in the heating phase, the control may be performed to increase the number of times the first frequency is selected, when the first frequency is selected within the first range and the second frequency is selected within the second range.

Further, in the step S3300 of controlling the RF energy in the heating phase, the number of times the first frequency is selected may be increased when the first frequency is selected within the second range and the second frequency is selected within the third range.

Further, in the step S3300 of controlling the RF energy in the heating phase, the number of times the first frequency is selected may be increased when the first frequency is selected within the first range and the second frequency is selected within the third range.

Meanwhile, the step S3400 of controlling the RF energy in the holding phase be performed by adjusting the RF energy based on the pulse train having a large number of high frequencies among the multiple frequencies. The first frequency or the second frequency may be selected within the first range, the second range, or the third range.

In the step S3400 of controlling the RF energy in the holding phase, the control may be performed to increase the number of times the second frequency is selected, when the first frequency is selected within the first range and the second frequency is selected within the second range.

Further, in the step S3400 of controlling the RF energy in the holding phase, the control may be performed to increase the number of times the second frequency is selected, when the first frequency is selected within the second range and the second frequency is selected within the third range.

Further, in the step S3400 of controlling the RF energy in the holding phase, the control may be performed to increase the number of times the second frequency is selected, when the first frequency is selected within the first range and the second frequency is selected within the third range.

Figure 20:
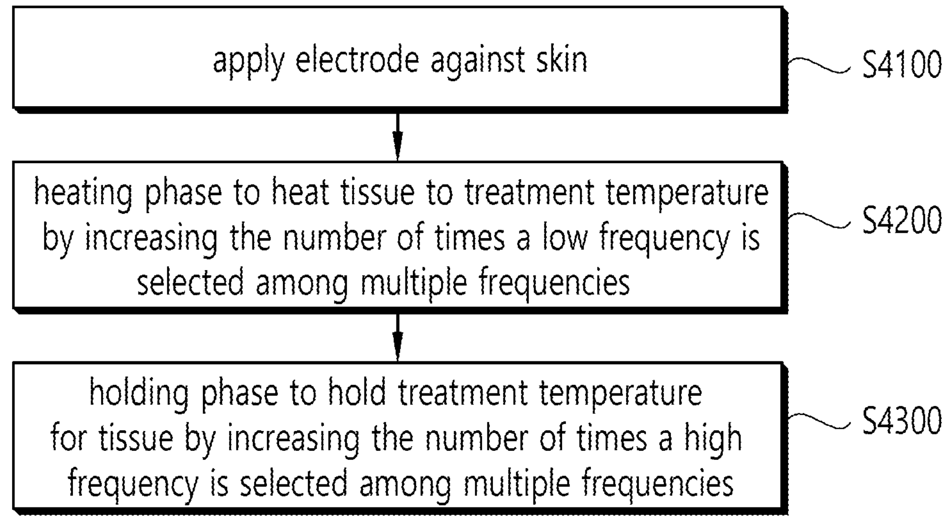
FIG. 20 is a flowchart of a treatment method of denaturing tissue with RF energy having multiple frequencies according to a sixth embodiment of the disclosure.

FIG. 20 is a flowchart of a treatment method of denaturing tissue with RF energy having multiple frequencies according to a sixth embodiment of the disclosure.

Referring to FIG. 20, the treatment method of denaturing tissue with RF energy having multiple frequencies according to the sixth embodiment of the disclosure may include steps of applying an electrode for delivering the RF energy against skin tissue S4100, delivering the RF energy from the electrode to the tissue, and treating dermis and/or subcutis by delivering the RF energy adjusted to have multiple frequencies selected within the first range, the second range or the third range to the skin tissue. Here, the step S4100 of applying the electrode for delivering the RF energy to the skin tissue and the step of delivering the RF energy from the electrode to the tissue may be performed as described above in the third embodiment.

The step of treating the dermis and/or the subcutis by delivering the RF energy to the skin tissue may be performed by selecting frequencies from two ranges, and adjusting the RF energy to have the selected frequencies. The step of treating the dermis and/or the subcutis comprises the step of heating phase and the step of holding phase.

The step of heating phase S4200 may be performed by heating the tissue while adjusting the RF energy based on the pulse train with a large number of times the low frequencies among the multiple frequencies. Here, the first frequency or the second frequency may be selected as the multiple frequencies within the first range, the second range, or the third range.

In this case, the adjustment from the first frequency to the second frequency may have a tendency to increase the frequency.

On the other hand, the adjustment from the first frequency to the second frequency may have a tendency to decrease the frequency.

Further, according to the sixth embodiment, the pulse train is configured such that the RF energy is regulated to have the frequency selected from each range, thereby delivering the RF energy adjusted based on the pulse train to heat the tissue.

In the step of heating phase S4200, the tissue may be heated to a treatment temperature by increasing the number of times the first frequency is selected, when the first frequency is selected within the first range and the second frequency is selected within the second range.

Further, in the step of heating phase S4200, the tissue may be heated to a treatment temperature by increasing the number of times the first frequency is selected, when the first frequency is selected within the second range and the second frequency is selected within the third range.

Further, in the step of heating phase S4200, the tissue may be heated to a treatment temperature by increasing the number of times the frequency is selected from the first range, when the first frequency is selected within the first range and the second frequency is selected within the third range.

In the step of holding phase S4300 according to an embodiment, the treatment temperature for the tissue is held by adjusting the RF energy based on the pulse train having a large number of high frequencies among the multiple frequencies. Here, the first frequency or the second frequency may be selected within the first range, the second range, or the third range.

In the step of holding phase S4300, the number of times the second frequency is selected may be increased when the first frequency is selected within the first range and the second frequency is selected within the second range.

Further, in the step of holding phase S4300, the number of times the second frequency is selected may be increased when the first frequency is selected within the second range and the second frequency is selected within the third range.

Further, in the step of holding phase, the number of times the second frequency is selected may be increased when the first frequency is selected within the first range and the second frequency is selected within the third range.

As described above, the treatment apparatus for denaturing tissue using RF energy having the multiple frequencies according to the disclosure, the control method thereof, and the treatment method using the same have effects on increasing a treatment efficiency because skin treatment is performed using the RF energy having various frequencies different in depth of delivering the energy into the tissue.

What is claimed is:

1. A treatment apparatus for denaturing tissue using radio frequency (RF) energy, the treatment apparatus comprising:

a main body comprising a RF source;

a handpiece connected to the main body, and comprising an electrode at one side to deliver the RF energy received from the RF source to skin; and a controller controlling the RF source to deliver the RF energy having multiple frequencies to the electrode, wherein the controller controls the RF source to generate RF energy having a first frequency or RF energy having a second frequency, and the controller performs control by dividing time of delivering the RF energy into a heating phase and a holding phase.

2. The treatment apparatus of claim 1, wherein the controller selects the first frequency and the second frequency within a first range, a second range or a third range.

3. The treatment apparatus of claim 2, wherein the second range is wider than the first range.

4. The treatment apparatus of claim 3, wherein the third range is wider than the second range.

5. The treatment apparatus of claim 4, wherein the second range is 1.1 or 5 times the first range.

6. The treatment apparatus of claim 5, wherein the third range is 2 to 10 times the second range.

7. The treatment apparatus of claim 1, wherein the controller increases a number of times a frequency is selected from a low-frequency range between two selected ranges in the heating phase.

8. The treatment apparatus of claim 1, wherein the controller increases a number of times a frequency is selected from a high-frequency range between two selected ranges in the holding phase.

9. The treatment apparatus of claim 1, wherein the controller performs control to increase a pulse width for delivering the RF energy at a frequency selected from a low-frequency range between two selected ranges in the heating phase.

10. A control method of a treatment apparatus for denaturing tissue using radio frequency (RF) energy, the control method comprising:

generating the RF energy from an RF generator;

delivering the RF energy to an electrode; and controlling the RF energy at multiple frequencies, wherein the controlling the RF energy comprises delivering RF energy having a first frequency and delivering RF energy having a second frequency, wherein the controlling the RF energy comprises selecting the first frequency and the second frequency within a first range, a second range or a third range, and wherein the controlling the RF energy comprises heating-phase control that regulates the RF energy along a pulse train, with a frequency selection count of a lower one of the selected first and second frequencies exceeding that of a higher one of the selected first and second frequencies.

11. The control method of claim 10, wherein the controlling the RF energy comprises:

selecting the first frequency from the first range, and selecting the second frequency from the second range, or selecting the first frequency from the second range, and selecting the second frequency from the third range, or selecting the first frequency from the first range, and selecting the second frequency from the third range.

12. The control method of claim 10, wherein the controlling the RF energy comprises:

selecting the first frequency from the third range, and selecting the second frequency from the second range, or selecting the first frequency from the second range, and selecting the second frequency from the first range, or selecting the first frequency from the third range, and selecting the second frequency from the first range.

13. A control method of a treatment apparatus for denaturing tissue using radio frequency (RF) energy, the control method comprising:

generating the RF energy from an RF generator;

delivering the RF energy to an electrode; and controlling the RF energy at multiple frequencies, wherein the controlling the RF energy comprises delivering RF energy having a first frequency and delivering RF energy having a second frequency, wherein the controlling the RF energy comprises selecting the first frequency and the second frequency within a first range, a second range or a third range, and wherein the controlling the RF energy comprises holding-phase control that regulates the RF energy along a pulse train, with a frequency selection count of a higher one of the selected first and second frequencies exceeding that of a lower one of the selected first and second frequencies.

14. A treatment method of denaturing tissue using radio frequency (RF) energy, the treatment method comprising:

applying an electrode for delivering the RF energy against skin tissue;

delivering the RF energy from the electrode to tissue; and treating dermis and/or subcutis by delivering the RF energy having multiple frequencies to the skin tissue, wherein the treating the dermis and/or the subcutis comprises a heating phase to heat tissue to a treatment temperature by increasing a number of times a low frequency is selected among the multiple frequencies.

15. The treatment method of claim 14, wherein the treating the dermis and/or the subcutis by delivering the RF energy to the skin tissue comprises delivering RF energy having a first frequency and delivering RF energy having a second frequency.

16. The treatment method of claim 15, wherein the treating the dermis and/or the subcutis by delivering the RF energy to the skin tissue is performed by selecting the first frequency and the second frequency within a first range, a second range or a third range.

17. The treatment method of claim 16, wherein the treating the dermis and/or the subcutis by delivering the RF energy to the skin tissue is performed by:

selecting the first frequency from the first range, and selecting the second frequency from the second range, or selecting the first frequency from the second range, and selecting the second frequency from the third range, or selecting the first frequency from the first range, and selecting the second frequency from the third range.

18. The treatment method of claim 17, wherein the treating the dermis and/or the subcutis by delivering the RF energy to the skin tissue comprises adjusting the frequency of the RF energy by:

selecting the first frequency from the third range, and selecting the second frequency from the second range, or selecting the first frequency from the second range, and selecting the second frequency from the first range, or selecting the first frequency from the third range, and selecting the second frequency from the first range.

19. A treatment method of denaturing tissue using radio frequency (RF) energy, the treatment method comprising:

applying an electrode for delivering the RF energy against skin tissue;

delivering the RF energy from the electrode to tissue; and treating dermis and/or subcutis by delivering the RF energy having multiple frequencies to the skin tissue, wherein the treating the dermis and/or the subcutis comprises a holding phase to hold the treatment temperature for tissue by increasing a number of times a high frequency is selected among the multiple frequencies.

* * * * *